(12) United States Patent
Huber et al.

(10) Patent No.: US 6,962,717 B1
(45) Date of Patent: Nov. 8, 2005

(54) PHARMACEUTICAL COMPOSITIONS

(75) Inventors: Gerald Huber, Ohringen (DE); Peter Gruber, Freiburg (DE)

(73) Assignee: Disphar International B.V., Hengelo Gld. (NL)

(*) Notice: Subject to any disclaimer, the term of this patent is extended or adjusted under 35 U.S.C. 154(b) by 0 days.

(21) Appl. No.: 09/890,104

(22) PCT Filed: Jan. 29, 1999

(86) PCT No.: PCT/IB99/00180

§ 371 (c)(1),
(2), (4) Date: Oct. 16, 2001

(87) PCT Pub. No.: WO00/44353

PCT Pub. Date: Aug. 3, 2000

(51) Int. Cl.⁷ ............ A61K 9/14; A61K 9/22; A61K 9/52; A61K 9/28; A61K 9/46
(52) U.S. Cl. .......... 424/490; 424/435; 424/436; 424/451; 424/458; 424/464; 424/465; 424/466; 424/467; 424/468; 424/474; 424/479; 424/489; 424/490; 424/494; 424/497
(58) Field of Search ............ 424/489, 490, 424/464, 451, 435, 436, 458, 465, 466, 467, 424/468, 474, 479, 494, 497

(56) References Cited

U.S. PATENT DOCUMENTS

| | | |
|---|---|---|
| 4,540,685 A | 9/1985 | Bauer |
| 4,713,248 A | 12/1987 | Kjornaes et al. |
| 5,013,727 A | 5/1991 | Halskov |
| 5,178,868 A * | 1/1993 | Malmqvist-Granlund et al. .......... 424/490 |
| 5,316,774 A | 5/1994 | Eury et al. |
| 5,476,667 A | 12/1995 | Kristensen et al. |
| 5,505,966 A | 4/1996 | Edman et al. |
| 5,580,580 A * | 12/1996 | Masterson et al. .......... 424/490 |
| 5,607,695 A | 3/1997 | Ek et al. |
| 5,716,648 A | 2/1998 | Halskov et al. |

FOREIGN PATENT DOCUMENTS

| | | |
|---|---|---|
| EP | 0 040 590 | 11/1981 |
| EP | 0 148 811 | 7/1985 |
| EP | 0 212 745 | 3/1987 |
| EP | 0 220 143 | 4/1987 |
| EP | 0 239 361 | 9/1987 |
| EP | 0 365 947 | 5/1990 |
| EP | 0 453 001 | 10/1991 |
| EP | 0 671 167 | 9/1995 |
| EP | 0 671 168 | 9/1995 |
| GB | 2134785 | 8/1984 |
| WO | WO 83/00435 | 2/1983 |
| WO | WO 91/18590 | 12/1991 |
| WO | WO 91/19483 | 12/1991 |
| WO | WO 92/09270 | 6/1992 |
| WO | WO 92/14452 | 9/1992 |
| WO | WO 92/16206 | 10/1992 |
| WO | WO 97/23199 | 7/1997 |
| WO | WO 97/25980 | 7/1997 |
| WO | WO 98/20858 | 5/1998 |

* cited by examiner

*Primary Examiner*—James M. Spear
(74) *Attorney, Agent, or Firm*—Leydig, Voit & Mayer, Ltd.

(57) ABSTRACT

A pharmaceutical composition for slow release of active ingredient in the gastrointestinal tract, comprising a plurality of active ingredient-containing particles coated with a material insoluble in gastric and intestinal juices, where the particles have as core a homogeneous mixture comprising an active pharmaceutical ingredient and a polymer insoluble in gastric and intestinal juices, with an average internal pore diameter not exceeding 35 μm, makes efficient and pH-independent delaying of release possible even with comparatively small amounts of polymer. It is additionally distinguished by a long shelf life and is particularly suitable also for nonspherical particles.

21 Claims, No Drawings

PHARMACEUTICAL COMPOSITIONS

This is the national phase of PCT/IB99/00180, filed Jan. 29, 1999, the disclosure of which is incorporated by reference.

The invention relates to improved delayed-release formulations for releasing active pharmaceutical ingredients such as, for example, 5-aminosalicylic acid in the gastrointestinal tract, preferably in the intestinal tract or colon, and to a process for producing such formulations.

5-Aminosalicylic acid formulations which can be administered orally for the treatment of ulcerative colitis and Crohn's disease have been disclosed in WO-A-81/02671. The tablet formulation disclosed therein was obtained by granulating 250 g of 5-aminosalicylic acid with a solution of 25 g of polyvinylpyrrolidone in isopropanol, subsequently coating the dried granules with 45 g of ethylcellulose, mixing the coated granules with 3 g of sodium stearate, 27 g of talc and 300 g of granules composed of microcrystalline cellulose, potato starch and polyvinylpyrrolidone, and compressing the mixture to tablets with a tablet weight of 650 mg and an active ingredient content of 250 mg. Such tablets are commercially available under the name Pentasa® (Ferring, Denmark). However, the disadvantages of this formulation are the relatively high proportion of excipients, over 60% by weight, and the low active ingredient content compared with the daily doses of about 1.5–4.5 g which are customary at present. In addition, granule particles are easily damaged during the tableting and thus alter the active ingredient release characteristics.

Besides this, a number of proposals have been disclosed in the attempt to achieve a more targeted or more controlled release of active ingredients in the intestinal tract or other advantages.

For example, WO-A-83/00435 discloses compositions which can be administered orally and which are coated with an anionic polymer which is insoluble below pH 7 but is soluble in the colon, wherein capsules or tablets containing 5-aminosalicylic acid, prednisolone or indomethacin and provided with a coating containing Eudragit S100 are described. The disclosed drug forms are coated capsules or coated tablets, i.e. monolithic drug forms. Release is said to take place selectively in the colon, for which purpose coating membranes which have a layer thickness of 60–150 μm and which can as yet be produced only at great cost are necessary.

The possibility of coating 5-aminosalicylic acid formulations to be resistant to gastric juice is likewise mentioned in WO-A-92/16206 and DE-A-31 51 196. The latter disclosure relates to readily soluble pharmaceutical preparations obtained by mixing 5-aminosalicylic acid with basic excipients and/or buffer mixtures. By contrast, WO-A-94/28911 proposes a composition containing a pH-regulating, essentially insoluble, alkaline material and, if required, having an enteric coating, and indicates as example a tablet formulation obtained from calcium carbonate granules coated with Eudragit L12.5P by mixing and tableting together with ethylcellulose-coated 5-aminosalicylic acid granules.

EP-A-0 671 168 discloses an oral composition for controlled release in the intestinal tract, with production of a press-coated tablet with an active ingredient-containing core. The coating contains polymer powder leading to resistance to gastric juice. However, the production of press-coated tablets is costly and requires special tablet presses. A similar method for producing a monolithic drug form resistant to gastric juice is also described in EP-A-0 671 167, but in this case a pH-independently water-soluble polymer is used for the coating, and then the coated tablet is also coated with an enteric polymer film.

In addition, the combination of enteric and insoluble materials in a coating layer has also been proposed previously. For example, EP-A-0 040 590 describes compositions which can be administered orally and comprise an active ingredient-containing core and a coating, the latter containing an anionic acrylic polymer which is soluble only above pH 5.5 and a water-insoluble quaternary ammonium-substituted acrylic polymer in the ratio of 10-85:90-15 by weight and, in addition, preferably a fatty alcohol or a fatty acid as plasticizer. Although WO-A-92/14452 discloses a capsule formulation for selective release of active ingredient in the intestine, in which both the granules present in the capsule and the capsule itself are coated with a material soluble in intestinal juice, it is possible, as mentioned, if required for the coating of the granules to contain an enteric material mixed with a neutral, insoluble but permeable polymer. The production of this drug form is costly, and it leads to a single unit dosage form whose residence time in the stomach may be subject to large variations in time.

By contrast, GB-A-2 134 785 discloses a slow-release formulation of pinacidil which comprises two types of pellets, the first type of pellet being coated with a material which is insoluble but permeable in the gastrointestinal tract, and the second type of pellet being coated with a material which is of low solubility at low pH but is soluble at pH values above 5–7.5. The pellets are produced by spraying an active ingredient suspension onto nonpareils (neutral pellets) and would be unsuitable for compression to a tablet form.

WO-A-92/09270 proposes a process which is said to make it possible to use an extrudate directly in the production of dosage forms, and in which a moist composition of active ingredient and excipients is extruded, and the extrudate is coated with a water-insoluble material. The extrudate must for this purpose contain a relatively large amount of excipient and would likewise be insufficiently mechanically stable for compression to tablets.

WO-A-85/03437 describes "multiple units" formulations with controlled release, in which active ingredient-containing particles (crystals or extruded pellets) are coated with an essentially water-insoluble but water-diffusable coating which may consist of one or two layers, where the inner or single layer has a homogeneous combination of a water-dispersible film-forming agent and of a polymeric, preferably water-soluble, substance which is intended to impart plastic deformability to the coating (and thus to prevent significant changes in the release characteristics through compression to tablets), and the optional outer layer contains a film-forming agent which is intended to prevent adhesion between the particles at elevated temperature and to improve the flowability. However, the coated particles with a low excipient content are insufficiently mechanically stable for compression to tablets.

In addition, various pharmaceutical formulations having both an enteric and an insoluble coating have also been proposed. For example, EP-A-0 148 811 describes formulations of active ingredients such as quinidine sulfate which are said to make improved release possible, irrespective of the solubility of the active ingredient, and in which granules of active ingredient in the form of a weak acid or base and excipients such as lactose, mannitol etc. are coated with a diffusion membrane composed of ethylcellulose and/or a copolymer of polyethyl methacrylate-methyl methacrylate-trimethylammoniumethyl methacrylate chloride, and, in addition, with an outer layer of at least one anionic polymer and/or a fatty acid with a pKa of 4.5 to 7. The outer layer is intended to protect from attack by gastric juice, while the inner membrane is intended to afford slow but controlled release, the intention being to release 80–90% of the active ingredient in a constant, pH-independent manner within 7–10 hours. A formulation with an active ingredient-containing core, an inner coating which is of low solubility in intestinal juice and is composed of ethylcellulose, hydroxypropylcellulose or carboxymethylcellulose and an outer enteric coating is also proposed in EP-A-0 239 361 for aspirin.

By contrast, EP-A-0 212 745 describes active ingredient particles in which the core, containing a propionic acid derivative as active ingredient, is coated with an inner coating of enteric acrylic polymer or copolymer and an outer coating of methacrylic acid polymer or copolymer which is insoluble in gastric and intestinal juices. It is intended in this way to compensate the decrease in the coating thickness by the decrease in the surface area of the particles and thus achieve constant release.

According to EP-A-0 453 001, moreover, controlled release in the intestine, especially in the terminal part of the ileum and colon, is said to be achieved by coating particles of an antiinflammatory agent with at least two membranes, one of which is soluble at pH$\geq$5.5 and the other is insoluble at this pH but permeable for intestinal fluids.

WO-A-92/00732 chose another route inasmuch as the use of materials such as pectins which are selectively degradable by enzymes normally occurring in the colon was proposed for producing colon-selective compositions. The disclosed compositions comprise a matrix core in which the active ingredient is dispersed, and a coating, and both the matrix core and the coating are intended to be enzymatically degradable.

WO-A-97/23199 attempted on the other hand to achieve advantageous release characteristics for 5-aminosalicylic acid by choosing certain excipients in combination with an optimal geometric shape of granule particles, and to ensure the bioavailability thereof both in the small intestine and in the large intestine. The disclosed granule particles have a core containing 5-aminosalicylic acid and a so-called spheronizing agent, preferably microcrystalline cellulose, and a coating of a semipermeable polymer, preferably ethylcellulose. In addition, the granule particles are intended to be essentially spherical and have a so-called aspect ratio, which is defined as the ratio of the longest to the shortest dimension of the particles, of 1.00–1.25. No coating insoluble in gastric and intestinal juices is incorporated in the particle matrix itself, and the described particles are moreover not very mechanically stable.

The production of spherical particles has also been described in WO-A-92/06679, but in this case a melt-granulation process was proposed, in which a mixture containing active ingredient in cohesive form and a binder with a melting point between 40° C. and 100° C. is processed mechanically, with input of energy, in such a way that the binder melts and the mixture is granulated to form spherical pellets.

Thus, in the prior art, it has mainly been attempted to avoid release in the stomach by application of a coating resistant to gastric juice, or to improve the delaying of release by producing spherical particles or suitably combining coating materials. However, the latter requires additional excipients and/or process measures, while the use of an enteric coating does not in every case ensure selective release of active ingredient at the desired site in the gastrointestinal tract, because the pH values in the gastrointestinal tract may in some cases vary considerably from patient to patient. In addition, the residence time of tablets in the stomach and their transit time through the intestinal tract and the colon may, as is well known, be subject to great variations, which likewise makes targeted release difficult.

The invention is therefore based on the object of providing a pharmaceutical composition for slow release of active ingredient in the gastrointestinal tract, which substantially avoids the disadvantages mentioned and which can be produced at reasonable cost and with high reproducibility. Another object of the present invention is to provide a pharmaceutical composition which permits slow release of active ingredient in the intestinal tract even when the active ingredient content is high and the excipient content is only low.

This object is achieved according to the invention by a pharmaceutical composition for slow release of active ingredient in the gastrointestinal tract, comprising a plurality of coated active ingredient-containing particles which have an active ingredient-containing core and a coating comprising a polymer insoluble in gastric and intestinal juices, where the active ingredient-containing core of the coated particles is a homogeneous mixture comprising an active pharmaceutical ingredient and a polymer insoluble in gastric and intestinal juices, and has an average internal pore diameter not exceeding 35 $\mu$m.

The coated active ingredient-containing particles of the composition of the invention have as core a compacted mixture containing active pharmaceutical ingredient and polymer insoluble in gastric and intestinal juices. The compaction is manifested by a decrease in the average internal pore diameter and the pore volume or porosity and can therefore best be characterized by average internal pore diameter and/or the porosity.

The internal pore diameter and the porosity of the active ingredient-containing cores of the composition of the invention can be determined using a Quantachrome or Micromeritics mercury porosimeter in a pressure range from 1000 to 4000 bar. The values stated for the purposes of the present invention relate in each case to measurements with a Quantachrome Poremaster (supplied by Quantachrome, Odelzhausen, Germany) at 1000 to 4000 bar. The average diameter of the pores is obtained in this case from the equilibrium pressure at which mercury penetrates into the pores, the relation being described by the Washburn equation (cf.: Dr. G. Huber, Thesis 1993, Freie Universität Berlin, Faculty of Pharmacy).

The compaction of the invention, which is described below, of the homogeneous mixture comprising active pharmaceutical ingredient and polymer insoluble in gastric and intestinal juices significantly reduces the porosity thereof and the average diameter of the internal pores. Whereas the average internal pore diameters with conventional matrix granules are usually up to about 100 $\mu$m, the active ingredient-containing cores compacted according to the invention have an average internal pore diameter which expediently does not exceed about 35 $\mu$m and preferably does not exceed about 20 $\mu$m. The porosity is usually reduced by about 10% with the compaction of the invention. The percent porosity is derived from the bulk density $\rho e$ (apparent density, determined by mercury porosimetry) and the true density $\rho a$ (solid density, determined by helium pycnometry) in accordance with the relation: porosity $P=100.(1-\rho e/\rho a)$. The corresponding values for conventional matrix granules are typically about 30%, whereas they do not exceed about 27%, for example about 10 to 25%, for the active ingredient-containing cores compacted according to the invention. In addition, the solid density of the active ingredient-containing cores is increased by the compaction of the invention usually by at least about 10%.

The composition of the invention is particularly suitable for targeted active ingredient release in the intestinal tract and, in particular, in the colon. However, in some cases it is desired for release of active ingredient to start even in the stomach, which can likewise be achieved with the composition of the invention. For example, it is desired in a few cases on treatment of Crohn's disease at a high location with 5-aminosalicylic acid that active ingredient be released in the lower part of the stomach in order to achieve an optimal effect in the short duodenal tract.

The composition of the invention has the advantage that the release of active ingredient takes place very substantially in a pH-independent manner and thus effects of biological differences between individual patients can be avoided almost completely. In addition, the coated active ingredient-containing particles can be administered as such or, preferably, in tablets or other dosage forms which disintegrate rapidly in the stomach and release the coated active ingredient-containing particles. Since the coated active ingredient-containing particles have a particle size (i.e. maximum dimension) of, preferably, about 0.1–3.0 mm, in particular about 0.2–2.5 mm and particularly preferably about 0.3–2.0 mm, it is ensured in every case that they leave the stomach very quickly through the pylorus. The large variations in the residence time in the stomach and the transit time through the intestinal tract and the colon, which occur with delayed-release tablets owing to their nature, are therefore avoided with the composition of the invention. The multiple unit pharmaceutical dosage form of the invention thus avoids, simply for this reason and moreover because of its special type of delaying release, the possibility of release of significant amounts of active ingredient even in the stomach, which is why a coating resistant to gastric juice can be dispensed with. It therefore also allows that even without an enteric coating, a targeted and moreover pH-independent control of release over up to 8 hours or else, if desired, over a longer period.

The release delaying in the composition of the invention takes place due to a combination of at least three measures, each of which contributes to delaying the release of active ingredient, namely by mixing the active ingredient with a polymer insoluble in gastric and intestinal juices (i.e. through formation of a particle matrix), through the small pore size, which is related to a corresponding compaction of the core material, and by coating with a polymer insoluble in gastric and intestinal juices. This method has the advantage inter alia that the release delaying is substantially independent of the shape and size of the particles and that it is therefore also possible to use nonspherical particles or particles differing in size. It has moreover emerged that very efficient release delaying is possible in this way even with small amounts of insoluble polymer and therefore delayed release formulations with a very high content of up to about 97% by weight active ingredient are possible. In addition, the type of release delaying of the invention does not depend on a possible external phase (e.g. tablet excipients), and the release delaying of the particles is, in contrast to previously disclosed formulations, not significantly impaired by compression to tablets either, because the highly compacted, lacquered matrix particles used according to the invention are very mechanically stable. The type of release delaying of the invention moreover has the advantage that perfectly divisible pharmaceutical forms, for example divisible delayed-release tablets (e.g. with score) are possible because the release delaying is unaffected by the division. It has additionally been found that the compositions of the invention are less affected by aging and temperature variations and therefore no significant changes in the release properties are to be observed even after prolonged storage.

The present invention therefore permits the production of improved delayed-release forms which moreover can be obtained at reasonable cost and with high reproducibility.

The formulation of the invention is suitable for administering in principle any active pharmaceutical ingredients which are to be released preferably in the intestine and/or colon and, in particular, those which can advantageously be administered in delayed-release form, such as antidiabetics, analgesics, antiinflammatory agents, antirheumatic agents, antihypotensives, antihypertensives, psychopharmaceuticals, tranquilizers, antiemetics, muscle relaxants, glucocorticoids, agents for treating ulcerative colitis or Crohn's disease, antiallergics, antibiotics, antiepileptics, anticoagulants, antimycotics, antitussives, arteriosclerosis remedies, diuretics, enzymes, enzyme inhibitors, gout remedies, hormones and their inhibitors, cardiac glycosides, immunotherapeutics and cytokines, laxatives, lipid-lowering agents, migraine remedies, mineral preparations, otologicals, antiparkinson agents, thyroid therapeutics, spasmolytics, platelet aggregation inhibitors, vitamins, cytostatics and metastasis inhibitors, phytopharmaceuticals, chemotherapeutics and amino acids.

Examples of suitable active ingredients are acarbose, beta-receptor blockers, non-steroidal antiinflammatory drugs, cardiac glycosides, acetylsalicylic acid, virustatics, aclarubicin, acylovir, cisplatin, actinomycin, alpha- and beta-sympathomimetics, omeprazole, allopurinol, alprostadil, prostaglandins, amantadine, ambroxol, amlodipine, methotrexate, 5-aminosalicylic acid, amitriptyline, amoxicillin, anastrozole, atenolol, azathioprine, balsalazide, beclomethasone, betahistine, bezafibrate, bicalutamide, diazepam and diazepam derivatives, budesonide, bufexamac, buprenorphine, methadone, calcium salts, potassium salts, magnesium salts, candesartan, carbamazepine, captopril, cefalosporins, cetirizine, chenodeoxycholic acid, ursodeoxycholic acid, theophylline and theophylline derivatives, trypsins, cimetidine, clarithromycin, clavulanic acid, clindamycin, clobutinol, clonidine, cotrimoxazole, codeine, caffeine, vitamin D and derivatives of vitamin D, colestyramine, chromoglicic acid, coumarin and coumarin derivatives, cysteine, cytarabine, cyclophosphamide, ciclosporin, cyproterone, cytarabine, dapiprazole, desogestrel, desonide, dihydralazine, diltiazem, ergot alkaloids, dimenhydrinate, dimethyl sulfoxide, dimethicone, dipyridamole, domperidone and domperidone derivatives, dopamine, doxazosine, doxorubizin, doxylamine, dapiprazole, benzodiazepines, diclofenac, glycoside antibiotics, desipramine, econazole, ACE inhibitors, enalapril, ephedrine, epinephrine, epoetin and epoetin derivatives, morphinans, calcium channel blockers, irinotecan, modafinil, orlistat, peptide antibiotics, phenytoin, riluzoles, risedronate, sildenafil, topiramate, macrolide antibiotices, estrogen and estrogen derivatives, gestagen and gestagen derivatives, testosterone and testosterone derivatives, androgen and androgen derivatives, ethenzamide, etofenamate, etofibrate, fenofibrate, etofylline, etoposide, famciclovir, famotidine, felodipine, fenofibrate, fentanyl, fenticonazole, gyrase inhibitors, fluconazole, fludarabine, flunarizine, fluorouracil, fluoxetine, flurbiprofen, ibuprofen, flutamide, fluvastatin, follitropin, formoterol, fosfomicin, furosemide, fusidic acid, gallopamil, ganciclovir, gemfibrozil, gentamicin, ginkgo, St John's wort, glibenclamide, urea derivatives as oral antidiabetics, glucagon, glucosamine and glucosamine derivatives, glutathione, glycerol and glycerol derivatives, hypothalamus hormones, goserelin, gyrase inhibitors, guanethidine, halofantrine, haloperidol, heparin and heparin derivatives, hyaluronic acid, hydralazine, hydrochlorothiazide and hydrochlorothiazide derivatives, salicylates, hydroxyzine, idarubicin, ifosfamide, imipramine, indometacin, indoramin, insulin, interferons, iodine and iodine derivatives, isoconazole, isoprenaline, glucitol and glucitol derivatives, itraconazole, ketoconazole, ketoprofen, ketotifen, lacidipine, lansoprazole, levodopa, levomethadone, thyroid hormones, lipoic acid and lipoic acid derivatives, lisinopril, lisuride, lofepramine, lomustine, loperamide, loratadine, maprotiline, mebendazole, mebeverine, meclozine, mefenamic acid, mefloquine, meloxicam, mepindolol, meprobamate, meropenem, mesalazine, mesuximide, metamizole, metformin, methotrexate, methylphenidate, methylprednisolone, metixen, metoclopramide, metoprolol, metronidazole, mianserin, miconazole, minocycline, minoxidil, misoprostol, mitomycin, mizolastine, moexipril, morphine and morphine derivatives, evening primrose, nalbuphine, naloxone, tilidine, naproxen, narcotine, natamycin, neostigmine, nicergoline, nicethamide, nifedipine, niflumic acid, nimodipine, nimorazole, nimustine, nisoldipine, adrenaline and adrenaline derivatives, norfloxacin, novaminsulfone, noscapine, nystatin, ofloxacin, olanzapine, olsalazine, omeprazole, omoconazole, ondansetron, oxaceprol, oxacillin, oxiconazole, oxymetazoline, pantoprazole, paracetamol, paroxetine, penciclovir, oral penicillins, pentazocin, pentifylline, pentoxifylline, perphenazine, pethidine, plant extracts, phenazone, pheniramine, barbituric acid derivatives, phenylbutazone, phenytoin, pimozide, pindolol, piperazine, piracetam, pirenzepine, piribedil, piroxicam, pramipexol, pravastatin, prazosin, procaine, promazine, propiverine, propranolol, propyphenazone, prostaglandins, protionamide, proxyphylline, quetiapine, quinapril, quinaprilate, ramipril, ranitidine, reproterol, reserpine, ribavirin, rifampicin, risperidone, ritonavir, ropinirol, roxatidine, roxithromycin, ruscogenin, rutoside and rutoside derivatives, sabadilla, salbutamol, salmeterol, scopolamine, selegiline, sertaconazole, sertindol, sertralion, silicates, simvastatin, sitosterol, sotalol, spaglumic acid, sparfloxacin, spectinomycin, spiramycin, spirapril, spironolactone, stavudine, streptomycin, sucralfate, sufentanil, sulbactam, sulfonamides, sulfasalazine, sulpiride, sultamicillin, sultiam, sumatriptan, suxamethonium chloride, tacrine, tacrolimus, taliolol, tamoxifen, taurolidine, tazaroten, temazepam, teniposide, tenoxicam, terazosin, terbinafine, terbutaline, terfenadine, terlipressin, tertatolol, tetracyclines, tetryzoline, theobromine, theophylline, butizine, thiamazole, phenothiazines, thiotepa, tiagabine, tiapride, propionic acid derivatives, ticlopidine, timolol, tinidazole, tioconazole, tioguanine, tioxolone, tiropramide, tizanidine, tolazoline, tolbutamide, tolcapone, tolnaftate, tolperisone, topotecan, torasemide, antiestrogens, tramadol, tramazoline, trandolapril, tranylcypromine, trapidil, trazodone, triamcinolone and triamcinolone derivatives, triamterene, trifluperidol, trifluridine, trimethoprim, trimipramine, tripelennamine, triprolidine, trifosfamide, tromantadine, trometamol, tropalpin, troxerutin, tulobuterol, tyramine, tyrothricin, urapidil, ursodeoxycholic acid, chenodeoxycholic acid, valaciclovir, valproic acid, vancomycin, vecuronium chloride, venlafaxine, verapamil, vidarabine, vigabatrin, viloxazine, vinblastine, vincamine, vincristine, vindesine, vinorelbine, vinpocetine, viquidil, warfarin, xantinol nicotinate, xipamide, zafirlukast, zalcitabine, zidovudine, zolmitriptan, zolpidem, zoplicone, zotepine and the like.

Examples of particularly preferred active ingredients are analgesics such as tramadol or morphine, agents for treating ulcerative colitis or Crohn's disease such as 5-aminosalicylic acid, corticosteroids such as budesonide, proton pump inhibitors such as omeprazole, virus statics such as acyclovir, lipid-lowering agents such as simvastatin or pravastatin, H2 blockers such as ranitidine or famotidine, antibiotics such as amoxicillin and/or clavulanic acid, and ACE inhibitors such as enalapril or amlodipine.

The active ingredients can, if required, also be used in the form of their pharmaceutically acceptable salts or derivatives, and in the case of chiral active ingredients it is possible to employ both optically active isomers and racemates or mixtures of diastereoisomers. If required, the compositions of the invention may also contain two or more active pharmaceutical ingredients.

The polymer which is mixed with the active ingredient, i.e. is present in the core of the coated particles, can in principle by any polymer which is essentially insoluble in gastric and intestinal juices and is suitable for matrix delaying of release. It is possible and preferred to use a polymer which is able to swell and/or be eroded in gastric and/or intestinal juices. Suitable materials, for example cellulose ethers such as ethylcellulose, cellulose esters such as cellulose acetate and, in particular, polymers and copolymers of acrylic and/or methacrylic esters are known to the skilled worker. Polymers with comparatively low permeability are generally preferred. Those particularly preferred are copolymers of acrylic and methacrylic esters in which the ester residues can preferably be methyl and ethyl groups; it is possible and preferred for them to have a small content of quaternary ammonium groups of up to about 1:20 in molar ratio to the other neutral (meth)acrylic esters. Examples of particularly suitable polymers are Eudragit® NE and, in particular, Eudragit® RS (Rohm & Haas, Japan). If required, it is also possible to use a mixture of two or more such polymers. If required, the mixture of active ingredient and polymer insoluble in gastric and intestinal juices may also contain polymers which are soluble in dilute acids and/or at neutral pH, or other excipients, in order to modify the release properties. Examples of suitable additions are Eudragit® E, Eudragit® L, Eudragit® S (Rohm & Haas, Japan) and shellac, polyethylene glycols, plasticizers and water-soluble polymers such as chitosans. It is generally preferred to use not more than up to about 35% by weight, based on the active ingredient-containing core, of such additions, and the amount of such additions—if present—can be, for example, about 1–20% by weight. Accordingly, the active ingredient-containing core can contain active ingredient and polymer insoluble in gastric and intestinal juices in a total amount of, preferably, at least about 65% by weight, for example about 80–99% by weight, or else, in particular, consist exclusively of active ingredient and polymer insoluble and gastric and intestinal juices.

The amount of polymer insoluble in gastric and intestinal juices in the core of the coated particles may vary depending on the required delaying of release and depending on the polymer and active ingredient used. The optimal amount can easily be established by the skilled worker in each case on the basis of his own experiments. However, the amount of polymer which generally suffices is only about 2–30% by weight, preferably about 4–15% by weight, based on the active ingredient, or about 2–18% by weight, preferably about 4–14% by weight, based on the coated particles, although larger amounts are perfectly possible too.

The polymer present in the coating of the coated particles can in principle likewise be any polymer which is essentially insoluble in gastric and intestinal juices and is suitable as coating material for delaying release. It is possible and preferred to use a polymer which is able to swell and/or be eroded in gastric and/or intestinal juice. Suitable materials, for example cellulose ethers such as ethylcellulose, cellulose esters such as cellulose acetate and, in particular, polymers and copolymers of acrylic and/or methacrylic esters are known to the skilled worker. Polymers with comparatively low permeability are generally preferred. Those particularly preferred are copolymers of acrylic and methacrylic esters in which the ester residues can preferably be methyl and ethyl groups; it is possible, if required, for them to have a small content of quaternary ammonium groups of up to about 1:20 in molar ratio to the other neutral (meth)acrylic esters, although in most cases polymers which contain no ammonium groups are preferred. Examples of particularly suitable polymers are Eudragit® RS and, in particular, Eudragit® NE (Rohm & Haas, Japan). If required, it is also possible to use two or more such polymers in the same or in separate coatings. If required, the coating may, besides polymer insoluble in gastric and intestinal juices, also contain materials soluble in gastric juice and/or soluble in intestinal juice, for example shellac, polyethylene glycols, chitosans or, preferably, enteric polymers such as Eudragit® L or Eudragit® S (Rohm & Haas, Japan), in order to modify the release properties. However, it is generally preferred to use not more than up to about 35% by weight, based on the total amount of coating materials, of such materials, and the amount of such materials—if present—can be, for example, about 1–20% by weight. Accordingly, the coating can contain polymer insoluble in gastric and intestinal juices in an amount of, preferably, at least about 65% by weight, for example about 80–99% by weight, or else, in particular, consist exclusively of one or more polymers insoluble in gastric and intestinal juices.

The amount of polymer insoluble in gastric and intestinal juices in the coating of the coated particles may likewise vary depending on the required delaying of release and depending on the polymer and active ingredient used. The optimal amount can easily be established by the skilled worker in each case on the basis of his own experiments. However, the amount of polymer which generally suffices is only about 2–30% by weight, preferably about 4–15% by weight, based on the active ingredient, or about 2–18% by weight, preferably about 4–14% by weight, based on the coated particles, although larger amounts are perfectly possible too.

If desired, the core and/or the coating of the coated particles may contain conventional excipients as additions, for example a plasticizer such as triethyl citrate and/or a lubricant such as talc and/or glycerol monostearate. It is possible and preferred in these cases for the core of the coated particles to contain a plasticizer such as triethyl citrate in an amount of, for example, about 0.1 to 3% by weight based on the coated particles, and/or for the coating to contain a lubricant such as talc in an amount of, for example, about 0.1 to 5% by weight based on the coated particles.

Further preferred aspects of the composition of the invention are evident from the following description of the production thereof.

The invention likewise relates to a process for producing the novel composition, which comprises the active pharmaceutical ingredient being mixed with a polymer insoluble in gastric and intestinal juices and compacted to a composition in such a way that the compacted composition has an average internal pore diameter not exceeding 35 $\mu$m, preferably not exceeding 20 $\mu$m, and comprises the compacted composition being comminuted to particles, and the particles being coated with a polymer insoluble in gastric and intestinal juices, and comprises, if required, the coated particles being converted into a suitable dosage form.

The individual process steps can be carried out by methods known per se. However, it is possible and preferred for the mixing of active ingredient and polymer insoluble in gastric and intestinal juices to take place by granulation by moistening the active ingredient which can, for example, be in the form of a powder, with a dispersion or solution of the polymer (e.g. a 30% strength aqueous dispersion of Eudragit® RS), and granulating and drying the mixture in a manner known per se. Suitable polymer dispersions or solutions are dispersions and solutions in water and/or organic solvents. Further possible additions or excipients can, depending on the nature of the materials, be either moistened together with the active ingredient or added as solution or dispersion. It is possible and preferred for the granulation to take place with high energy input, for example by stirring at high speed, in order to increase the bulk density, i.e. to compact the active ingredient/polymer mixture. Suitable for this purpose are, for example, the known vacuum granulators supplied by Colette (Great Britain), Zanchetta (Italy) and Bohle (Germany). The energy input therewith is preferably so high that the granules are warmed by at least about 1° C., for example about 1–5° C., during the moistening which lasts, for example, about 10–20 minutes. The subsequent drying can take place in a manner known per, e.g. in vacuo or by convection drying.

The subsequent compaction of the mixture (e.g. granules) composed of active ingredient, polymer insoluble in gastric and intestinal juices and any other additions can likewise take place in a manner known per se, for example using a roller compactor such as, for example, a Pharmapaktor L200/50P from Bepex Hosokawa (Japan) or a roll press of the type 250/100/3 from Gerteis (Switzerland). The gap between the rolls can be, for example, between 0.2 and 3.5 mm. It is possible and preferred for the pressure applied for the compaction to be at least about 5 kN, for example about 5–30 kN, per cm length of press. In addition, it is generally preferred to use a higher pressure for the compaction than for a possible later tableting. It is possible with these measures to eliminate virtually completely pores with an internal pore diameter of more than 35 $\mu$m, and to compact the active ingredient/polymer mixture so greatly that its density is at least 10%, frequently 50% or more, above the bulk density of the starting material.

The resulting compact, i.e. the compacted active ingredient/polymer mixture, can subsequently be comminuted in a manner known per se to the required particle size, which is possible and preferably in the range from about 0.1 to 3.0 mm. In a preferred variant this can take place by breaking the compact on a suitable screen, for example a rotating screen, and adjusting the compact particles to the required particle size. This usually results in irregularly shaped, nonspherical particles. As already mentioned above, however, the shape and size of the particles of the compositions of the invention have virtually no effect on their release characteristics, so that no separate measures are necessary to form approximately spherical particles. The characteristic number normally used to describe the shape factor of particles is the sphericity according to Wadell, which represents the ratio of the surface area of the sphere of the same volume to the actually measured surface area. Whereas ideally spherical particles have a sphericity of 1, it is possible and straightforward—in contrast to previously disclosed formulations—also to use according to the invention particles with a sphericity of, for example, less than 0.9 or else less than 0.8. A higher sphericity is, of course, not disadvantageous. Nevertheless, it can be said that a high sphericity is not necessary according to the invention, and that in most cases the majority (i.e. more than 50% of the particles) of the coated particles used according to the invention may have a sphericity of less than 0.9 or even of less than 0.8.

The coating of the compacted particles with a polymer insoluble in gastric and intestinal juices can likewise take place in a manner known per se, for example by drum coating or, preferably, by fluidized bed coating. It is possible and preferred for this to use an aqueous dispersion of the polymer, for example a 40% strength aqueous dispersion of Eudragit® NE. If required, other substances can be added to the coating material, for example chitosan, an enteric polymer, a lubricant such as talc or an antifoam. The drying of the coated particles can take place at the usual temperatures and, where appropriate in vacuo.

The resulting coated particles can, if required, be processed to tablets in a manner known per se and with use of conventional tablet excipients such as binders, disintegrants, lubricants and the like. These tablets are distinguished inter alia by the fact that the release rate is essentially independent of the pressure used for the tableting and of the hardness of the tablet, and that they can be divided without significantly changing the release characteristics. It is possible and preferred to use for the tableting an elastic, pressure-absorbing outer tablet phase which rapidly disintegrates in the stomach. Delayed release tablets which rapidly disintegrate in the stomach, e.g. within less than 30 seconds, are particularly desired when the residence time in the stomach is to be as short as possible. Particularly suitable tablet excipients have proved to be a combination of microcrystalline cellulose, water-soluble polyvinylpyrrolidone and crosslinked water-insoluble polyvinylpyrrolidone. It is possible and preferred in this case for the microcrystalline cellulose and the water-soluble polyvinylpyrrolidone initially to be processed to auxiliary granules and then compressed together with the coated particles and the crosslinked polyvinylpyrrolidone to give tablets. The auxiliary granules can be produced, for example, in a WSG fluidized bed granulator from Glatt (Switzerland) or an HKC fluidized bed granulator from BWI (Germany). The amount of tablet excipients based on the complete formulation can be, for example, about 3 to 90% by weight or more, in particular about 20 to 60% by weight. If required, the amount of tablet excipients can be kept very low, which is advantageous in particular with high-dose active ingredients, while larger amounts of excipients, of up to about 90% by weight or more, are normally used for low-dose active ingredients in order to obtain a customary tablet size. If required, it is possible according to the invention to obtain tablets with a high active ingredient content of more than 90% by weight or even more than 95% by weight with, nevertheless, good delaying of release. According to another preferred aspect, the coated active ingredient-containing particles obtainable according to the invention can also be compressed to tablets in particular with less than 3% by weight of tablet excipients based on the complete tablet formulation, or even completely without tablet excipients. A slight deterioration, occasionally occurring in this case, of the delaying of release can be compensated straightforwardly by a slightly larger amount of coating in the active ingredient-containing particles.

The coated particles can, if required, also be administered orally as such or be processed in a manner known per se to other administration forms such as sugar-coated tablets, capsules, film-coated tablets, disperse tablets, lingual disperse tablets, effervescent tablets, sachets, powders for reconstitution, suppositories and the like.

The invention is illustrated further by the following examples. The antifoam emulsion used in each case was simethicone emulsion USP, containing 28.5% by weight of dimethicone (a silicone oil), 1.5% by weight of silica, 3% by weight of methylcellulose, 0.1% by weight of sorbic acid and 66.9% by weight of water (data relating to the composition of the complete formulations refer in each case only to the solids content). Eudragit® RS30D is a 30% strength aqueous dispersion of Eudragit® RS, and Eudragit® NE40D is a 40% strength aqueous dispersion of Eudragit® NE (Rohm & Hass, Japan). Eudragit® E 12.5 is a 12.5% strength solution of Eudragit® E in isopropanol/acetone (60:40), and Eudragit® S 12.5 is a 12.5% strength solution of Eudragit® S in isopropanol (Rohm & Hass, Japan). Kollidon K90 (Hoechst, Germany) is a polyvinylpyrrolidone with a molecular weight of about 90000. Kollidon CL (Hoechst, Germany) is a crosslinked water-insoluble polyvinylpyrrolidone.

EXAMPLE 1

5-Aminosalicylic acid tablet formulation containing per tablet:

| | |
|---|---|
| 5-Aminosalicylic acid | 500.00 mg |
| Eudragit RS | 25.00 mg |
| Triethyl citrate | 5.00 mg |
| Compact particle, total | 530.00 mg |
| Eudragit NE | 23.85 mg |
| Talc | 12.67 mg |
| Simethicone Emulsion USP | 0.48 mg |
| Coated particles total | 567.00 mg |
| Microcrystalline cellulose | 144.06 mg |
| Kollidon K90 | 8.94 mg |
| Kollidon CL | 40.00 mg |
| Tablets total | 760.00 mg |

To produce 350000 tablets, 175 kg. of 5-aminosalicylic acid are moistened in a Roto P/F 400 l vacuum granulator from Zanchetta (Italy) with an aqueous dispersion of 29.167 kg of Eudragit RS30D (containing 8.750 kg of Eudragit RS), 1.750 kg of triethyl citrate and 7.65 g of water within 10–20 minutes and compacted with high energy input (by stirring at high speed, during which the mixture warms by 4° C.). The resulting granules are then dried by convection drying at 50–90° C. until the residual water content is less than 1% by weight. The dried granules are then compacted further using a type 250/100/3 roll press from Gerteis (Switzerland) applying a pressure of 15–20 kN per cm length of press and with a gap between the rolls of 2.0±0.5 mm. The ribbon resulting from the compaction is broken on a rotating screen, and the resulting compact is adjusted to a particle size of 0.6–1.25 mm.

This fractionated compact is then coated with an aqueous suspension of 20.869 kg of Eudragit NE40D (containing 8.348 kg of Eudragit NE), 4.435 kg of talc, 509.0 g of a 33% strength antifoam emulsion (Simethicone Emulsion USP) and 20.867 kg of water. In order to minimize the electrostatic charging during this process, further talc (a total of 2.765 kg) is periodically put on the compact.

In a type HKC fluidized bed granulator from BWI (Germany), 50.421 kg of microcrystalline cellulose are granulated with a solution of 3.129 kg of Kollidon K90 in 35.000 kg of water. The coated and fractionated compact (198.450 kg) is then mixed with the resulting granules (53.550 kg) and 14.000 kg of Kollidon CL and compressed under a pressure of 25–45 kN to circular tablets with a diameter of 13.5 mm, a height of 4.5 mm and a mass of 760 mg. The resulting tablets have a hardness of more than 0.8 N per mm$^2$ breakage area.

EXAMPLE 2

To investigate the release characteristics of tablets produced in a manner analogous to Example 1 from 5-aminosalicylic acid, the experiments described below were carried out. The active ingredient release was measured in each case using a Sotax AT7 (Paddle method) from Sotax (Switzerland) in accordance with the European Pharmacopoeia and US Pharmacopeia.

a) Tablets obtained in two batches with a maximum particle size of the coated active ingredient particles respectively of 1000 μm (batch I) and 700 μm (batch II) were investigated for their release rate at pH 1.2 (0.1 N hydrochloric acid). The results compiled in Table 1 show that the particle size has virtually no effect on release values for the formulation of the invention, while the release from conventional coated granules is usually dependent on the surface area and the particle size.

TABLE 1

| Time | Release [%] | |
|---|---|---|
| [min.] | Batch I (1000 μm) | Batch II (700 μm) |
| 30 | 24.9 | 25.3 |
| 60 | 38.8 | 38.9 |
| 90 | 49.7 | 49.7 |
| 120 | 58.8 | 58.3 |
| 150 | 66.5 | 65.7 |
| 180 | 72.9 | 72.0 |
| 210 | 78.2 | 77.4 |
| 240 | 82.5 | 81.7 | b) Tablets of batch I from section a) were kept at 50° C. for 24 h or 60° C. for 65 h, and then their release of active ingredient was investigated, comparing with non-heat-treated tablets, in ICH phosphate buffer pH 6.8. As the results compiled in Table 2 show, the release of active ingredient is also virtually unaffected by the nature and conditions of the heat treatment.

TABLE 2

| Time | Release [%] | | |
|---|---|---|---|
| [min.] | not heat treated | 24 h/50° C. | 65 h/60° C. |
| 30 | 19.2 | 18.7 | 19.0 |
| 60 | 34.5 | 33.4 | 34.0 |
| 90 | 47.2 | 45.6 | 46.4 |
| 120 | 57.6 | 55.7 | 56.7 |
| 150 | 66.2 | 64.2 | 65.2 |
| 180 | 73.0 | 71.1 | 72.1 |
| 210 | 78.6 | 76.9 | 77.8 |
| 240 | 82.8 | 81.2 | 82.1 | c) Tablets of batch I from section a) were halved and then their release of active ingredient was investigated, comparing with whole tablets, at pH 1.2 (0.1 N hydrochloric acid). The results compiled in Table 3 show that the delaying of release is not impaired by the halving of the tablets.

TABLE 3

| Time | Release [%] | |
|---|---|---|
| [min.] | Whole tablet | Half tablet |
| 30 | 24.9 | 24.0 |
| 60 | 38.8 | 38.2 |
| 90 | 49.7 | 49.0 |
| 120 | 58.8 | 58.1 |
| 150 | 66.5 | 65.7 |
| 180 | 72.9 | 71.8 |
| 210 | 78.2 | 77.4 |
| 240 | 82.5 | 81.4 | d) 3 batches of 5-aminosalicylic acid tablets with a tablet hardness respectively of 80 N, 120 N and 170 N (according to the hardness tester from Kraemer, Germany) were produced in a manner analogous to Example 1. As the release values in ICH phosphate buffer pH 6.8 which are compiled in Table 4 show, the release rate is also scarcely affected by the tablet hardness.

TABLE 4

| Time | Release [%] | | |
|---|---|---|---|
| [min.] | 80 N | 120 N | 170 N |
| 30 | 17.5 | 18.7 | 19.4 |
| 60 | 32.5 | 33.4 | 34.0 |
| 90 | 46.2 | 45.6 | 47.4 |
| 120 | 55.6 | 55.7 | 57.7 |
| 150 | 65.2 | 64.2 | 65.2 |
| 180 | 71.0 | 71.1 | 72.1 |
| 210 | 75.5 | 76.9 | 76.8 |
| 240 | 81.8 | 81.2 | 82.0 | e) 2 batches of 5-aminosalicylic acid tablets were produced in a manner analogous to Example 1 but with use of respectively 25% by weight and 50% by weight of external tablet excipients based on the complete tablet formulation. The release values at pH 1.2 (0.1 N hydrochloric acid) compiled in Table 5 show that the release of active ingredient is also scarcely affected by the amount of tablet excipients.

TABLE 5

| Time | Release [%] | |
|---|---|---|
| [min.] | 25% tablet excipients | 50% tablet excipients |
| 30 | 24.9 | 23.8 |
| 60 | 38.8 | 37.2 |
| 90 | 49.7 | 48.1 |
| 120 | 58.8 | 57.5 |
| 150 | 66.5 | 66.0 |
| 180 | 72.9 | 71.9 |
| 210 | 78.2 | 77.4 |
| 240 | 82.5 | 82.4 |

EXAMPLE 3

Tramadol hydrochloride tablet formulation containing per tablet:

| | |
|---|---:|
| Tramadol hydrochloride | 100.00 mg |
| Eudragit RS | 10.00 mg |
| Triethyl citrate | 2.00 mg |
| Compact particles total | 112.00 mg |
| Eudragit NE | 5.60 mg |
| Talc | 2.00 mg |
| Simethicone Emulsion USP | 0.66 mg |
| Coated particles total | 120.26 mg |
| Microcrystalline cellulose | 170.00 mg |
| Kollidon K90 | 14.74 mg |
| Kollidon CL | 15.00 mg |
| Tablets total | 320.00 mg |

To produce 350000 tablets, in a manner analogous to Example 1 35.0 kg of tramadol hydrochloride are moistened with an aqueous dispersion of 11.67 kg of Eudragit RS30D (containing 3.5 kg of Eudragit RS), 700 g of triethyl citrate and about 2.0 kg of water, granulated, dried at 80° C., compacted and fractionated (pressure 15–35 kN/cm, particle size 0.6–1.25 mm). A coating is applied to this compact in a manner analogous to Example 1 using 4.9 kg of Eudragit NE40D (containing 1.96 kg of Eudragit NE), 700 g of talc, 700 g of a 33% strength simethicone emulsion USP and 4.4 kg of water. This coated compact is then mixed in a manner analogous to Example 1 with 5.250 kg of Kollidon CL and granules composed of 59.5 kg of microcrystalline cellulose and 5.166 kg of Kollidon K90, and compressed to tablets with a mass of 320 mg.

It is possible in an analogous manner to obtain 420 mg tablets with a larger content of, for example, 200 mg of tramadol hydrochloride by use of a correspondingly smaller amount of granules composed of microcrystalline cellulose and Kollidon K90 for the tableting.

EXAMPLE 4

Morphine hydrochloride tablet formulation containing per tablet:

| | |
|---|---:|
| Morphine hydrochloride | 20.00 mg |
| Eudragit RS | 5.00 mg |
| Eudragit E | 0.50 mg |
| Triethyl citrate | 1.00 mg |
| Compact particles total | 26.50 mg |
| Eudragit NE | 5.00 mg |
| Talc | 1.00 mg |
| Simethicone emulsion USP | 0.33 mg |
| Eudragit S | 1.00 mg |
| Coated particles total | 33.83 mg |
| Microcrystalline cellulose | 51.50 mg |
| Kollidon K90 | 5.67 mg |
| Kollidon CL | 9.00 mg |
| Tablets total | 100.00 mg |

Production takes place in a manner analogous to Examples 1 and 2, although Eudragit E 12.5 is also added to the mixture of morphine hydrochloride, Eudragit RS and triethyl citrate for the granulation and, after the coating with Eudragit NE, talc and simethicone emulsion, the coated active ingredient-containing particles are also sprayed with Eudragit S 12.5.

EXAMPLE 5

5-Aminosalicylic acid tablet formulation containing per tablet:

| | |
|---|---:|
| 5-Aminosalicylic acid | 750.00 mg |
| Eudragit RS | 37.50 mg |
| Triethyl citrate | 7.50 mg |
| Compact particles total | 795.00 mg |
| Eudragit NE | 31.80 mg |
| Talc | 15.56 mg |
| Simethicone emulsion USP | 0.64 mg |
| Coated particles total | 843.00 mg |
| Kollidon CL | 50.00 mg |
| Tablets total | 893.00 mg |

Production takes place in a manner analogous to Example 1. It is also possible in an analogous manner to produce tablets without tablet excipients, i.e. without use of Kollidon CL in the tableting.

What is claimed is:

1. A pharmaceutical composition for slow release of active ingredient in the gastrointestinal tract, comprising a plurality of coated active ingredient-containing particles which have an active ingredient-containing core and a coating comprising a polymer insoluble in gastric and intestinal juices, where the active ingredient-containing core of the coated particles is a homogeneous mixture comprising an active pharmaceutical ingredient and a polymer insoluble in gastric and intestinal juices, and has an average internal pore diameter, measured by mercury porosimetry at 1000 to 4000 bar, not exceeding 35 $\mu$m.

2. A pharmaceutical composition for slow release of active ingredient in the gastrointestinal tract, comprising a plurality of coated active ingredient-containing particles which have an active ingredient-containing core and a coating comprising a polymer insoluble in gastric and intestinal juices, where the active ingredient-containing core of the coated particles is a homogeneous mixture comprising an active pharmaceutical ingredient and a polymer insoluble in gastric and intestinal juices, and has a percent porosity not exceeding 27%.

3. A composition as claimed in claim 1, wherein the polymer present in the core of the coated active ingredient-containing particles and/or the polymer present in the coating of the coated active ingredient-containing particles is a polymer which is able to swell and/or be eroded in gastric and/or intestinal juices.

4. A composition as claimed in claim 1, wherein the polymer present in the core of the coated active ingredient-containing particles and/or the polymer present in the coating of the coated active ingredient-containing particles is a cellulose ether, a cellulose ester or a polymer or copolymer of acrylic and/or methacrylic esters.

5. A composition as claimed in claim 1, wherein the core of the coated active ingredient-containing particles contains 2–30% by weight of polymer insoluble in gastric and intestinal juices, based on the active ingredient, and/or the coating of the coated active ingredient-containing particles contains 2–30% by weight of polymer insoluble in gastric and intestinal juices, based on the active ingredient.

6. A composition as claimed in claim 1, wherein the coated active ingredient-containing particles have a particle size of from 0.1 to 3.0 mm.

7. A composition as claimed in claim 1, wherein the majority of the coated particles have a sphericity according to Wadell of less than 0.9.

8. A composition as claimed in claim 1, wherein the active pharmaceutical ingredient is an active ingredient from the group of antidiabetics, analgesics, antiinflammatory agents, antirheumatic agents, antihypotensives, antihypertensives, psychopharmaceuticals, tranquilizers, antiemetics, muscle relaxants, glucocorticoids, agents for treating ulcerative colitis or Crohn's disease, antiallergics, antibiotics, antiepileptics, anticoagulants, antimycotics, antitussives, arteriosclerosis remedies, diuretics, enzymes, enzyme inhibitors, gout remedies, hormones and their inhibitors, cardiac glycosides, immunotherapeutics and cytokines, laxatives, lipid-lowering agents, migraine remedies, mineral preparations, otologicals, antiparkinson agents, thyroid therapeutics, spasmolytics, platelet aggregation inhibitors, vitamins, cytostatics and metastasis inhibitors, phytopharmaceuticals, chemotherapeutics and amino acids.

9. A composition as claimed in claim 1, wherein the active pharmaceutical ingredient is an active ingredient from the group of analgesics, agents for treating ulcerative colitis or Crohn's disease, corticosteroids, proton pump inhibitors, virus statics, lipid-lowering agents, H2 blockers, antibiotics and ACE inhibitors.

10. A composition as claimed in claim 1, wherein the active pharmaceutical ingredient is tramadol, morphine, 5-aminosalicylic acid, budesonide, omeprazole, acyclovir, simvastatin, pravastatin, ranitidine, famotidine, amoxicillin, clavulanic acid, enalapril, amlodipine or a pharmaceutically acceptable salt or derivative thereof.

11. A composition as claimed in claim 1, in the form of tablets, sugar-coated tablets, capsules, film-coated tablets, disperse tablets, lingual disperse tablets, effervescent tablets, sachets, powders for reconstitution or suppositories.

12. A composition as claimed in claim 1, in the form of tablets containing microcrystalline cellulose, water-soluble polyvinylpyrrolidone and crosslinked water-insoluble polyvinylpyrrolidone as tablet excipients.

13. A composition as claimed in claim 1 in the form of a divisible delayed release tablet.

14. A process for producing a pharmaceutical composition as claimed in claim 1, which comprises the active pharmaceutical ingredient being mixed with a polymer insoluble in gastric and intestinal juices and compacted to a composition in such a way that the compacted composition has an average internal pore diameter, measured by mercury porosimetry at 1000 to 4000 bar, not exceeding 35 µm, and comprises the compacted composition being comminuted to particles, and the particles being coated with a polymer insoluble in gastric and intestinal juices, and comprises, optionally, the coated particles being converted into a suitable dosage form.

15. A process for producing a pharmaceutical composition as claimed in claim 2, which comprises the active pharmaceutical ingredient being mixed with a polymer insoluble in gastric and intestinal juices and compacted to a composition in such a way that the compacted composition has a percent porosity not exceeding 27%, and comprises the compacted composition being comminuted to particles, and the particles being coated with a polymer insoluble in gastric and intestinal juices, and comprises, optionally, the coated particles being converted into a suitable dosage form.

16. A process as claimed in claim 14, wherein for mixing the active pharmaceutical ingredient with the polymer insoluble in gastric and intestinal juices the active ingredient is moistened with an aqueous and/or organic dispersion or solution of the polymer, and the mixture is granulated and dried.

17. A process as claimed in claim 14, wherein the compaction takes places under a pressure of at least 5 kN per cm length of press.

18. A composition as claimed in claim 2, wherein the polymer present in the core of the coated active ingredient-containing particles and/or the polymer present in the coating of the coated active ingredient-containing particles is a polymer which is able to swell and/or be eroded in gastric and/or intestinal juices.

19. A composition as claimed in claim 2, wherein the polymer present in the core of the coated active ingredient-containing particles and/or the polymer present in the coating of the coated active ingredient-containing particles is a cellulose ether, a cellulose ester or a polymer or copolymer of acrylic and/or methacrylic esters.

20. A composition as claimed in claim 2, wherein the core of the coated active ingredient-containing particles contains 2–30% by weight of polymer insoluble in gastric and intestinal juices, based on the active ingredient, and/or the coating of the coated active ingredient-containing particles contains 2–30% by weight of polymer insoluble in gastric and intestinal juices, based on the active ingredient.

21. A composition as claimed in claim 2, wherein the coated active ingredient-containing particles have a particle size of from 0.1 to 3.0 mm.

* * * * *